(12) United States Patent
Mayer et al.

(10) Patent No.: US 6,392,117 B1
(45) Date of Patent: *May 21, 2002

(54) BODY FITTING COMPOUND SANITARY NAPKIN

(75) Inventors: Katherine Louise Mayer, Newport, KY (US); Bruce William Lavash, West Chester; John Lee Hammons, Hamilton, both of OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/785,128

(22) Filed: Jan. 21, 1997

Related U.S. Application Data

(63) Continuation of application No. 08/636,711, filed on Apr. 23, 1996, now abandoned, which is a continuation of application No. 08/293,867, filed on Aug. 29, 1994, now abandoned.

(51) Int. Cl.[7] .......................... A61F 13/15; A61F 13/20
(52) U.S. Cl. ............. 604/378; 604/385.04; 604/385.16; 604/385.17; 604/387
(58) Field of Search ............................... 604/378, 385.1, 604/386–391, 400, 401, 402, 385.04, 385.16, 385.17

(56) References Cited

U.S. PATENT DOCUMENTS

| 2,043,325 A | * 6/1936 | Jackson, Jr. ................ 604/401 |
| 2,295,016 A | 9/1942 | Scribner |
| 2,331,355 A | 10/1943 | Strongson |
| 2,662,527 A | 12/1953 | Jacks ........................ 128/290 |
| 2,683,457 A | 7/1954 | Cunningham |
| RE24,137 E | * 4/1956 | Jacks ........................ 604/378 |
| 2,929,379 A | 3/1960 | Pulsen |
| 2,965,102 A | 12/1960 | Harwood |
| 3,115,877 A | * 12/1963 | Harwood ................. 604/385.1 |
| 3,183,909 A | 5/1965 | Roehr |
| 3,406,689 A | 10/1968 | Hicks et al. |
| 3,512,530 A | 5/1970 | Jones, Sr. |
| 3,528,422 A | * 9/1970 | Hodas ..................... 604/385.1 |
| 3,570,492 A | 3/1971 | Bettencourt |
| 3,654,929 A | 4/1972 | Nilsson et al. |

(List continued on next page.)

FOREIGN PATENT DOCUMENTS

| CA | 2 019 391 | 12/1990 | |
| DE | 2 029 766 | 6/1970 | .......... B32B/31/00 |
| EP | 0 426 197 A2 | 5/1991 | |
| EP | 0 525 778 A3 | 2/1993 | .......... A61F/13/15 |

(List continued on next page.)

Primary Examiner—Bruce Snow
(74) Attorney, Agent, or Firm—Matthew P. Fitzpatrick; Kevin C. Johnson; Steven W. Miller

(57) ABSTRACT

A compound sanitary napkin including a primary absorbent member and a secondary absorbent member. The primary absorbent member has a length and a width. The secondary absorbent member has a length and a width. The primary absorbent member and the secondary absorbent member have a common length. The primary absorbent member includes an absorbent core and a fluid pervious topsheet superposed on the absorbent core. The secondary absorbent member includes a fluid pervious topsheet, a fluid impervious backsheet joined to the topsheet and an absorbent element positioned between the topsheet and the backsheet. The primary absorbent member is affixed to the secondary absorbent member by union means. The primary absorbent member preferably exhibits a stationary resistance greater than or equal to 50 grams.

8 Claims, 10 Drawing Sheets

U.S. PATENT DOCUMENTS

| | | | |
|---|---|---|---|
| 4,019,517 A | * | 4/1977 | Glattman .................. 604/401 |
| 4,022,210 A | | 5/1977 | Glassman |
| 4,046,147 A | | 9/1977 | Berg |
| 4,195,634 A | * | 4/1980 | DiSalvo et al. .......... 604/385.1 |
| 4,340,058 A | | 7/1982 | Pierce et al. |
| 4,425,130 A | | 1/1984 | DesMarais ................ 604/389 |
| 4,433,972 A | | 2/1984 | Malfitano |
| 4,490,147 A | | 12/1984 | Pierce et al. |
| 4,505,707 A | * | 3/1985 | Feeney ..................... 604/389 |
| 4,576,597 A | * | 3/1986 | Hlaban ..................... 604/389 |
| 4,578,069 A | | 3/1986 | Whitehead et al. |
| 4,636,209 A | | 1/1987 | Lassen |
| 4,758,240 A | | 7/1988 | Glassman |
| 4,938,756 A | * | 7/1990 | Salek ....................... 604/401 |
| 5,057,096 A | | 10/1991 | Faglione |
| 5,092,860 A | | 3/1992 | Pigneul |
| 5,169,394 A | | 12/1992 | Jean |
| 5,171,302 A | | 12/1992 | Buell |
| B1 4,589,876 A | | 4/1993 | Ven Tilburg |
| 5,236,428 A | * | 8/1993 | Zajaczkowski ......... 604/385.1 |
| D342,785 S | | 12/1993 | Farrell |
| 5,267,992 A | | 12/1993 | Van Tilburg |
| 5,336,208 A | | 8/1994 | Rosenbluth et al. |
| 5,364,382 A | | 11/1994 | Latimer et al. |
| 5,391,160 A | | 2/1995 | Runeman et al. ........... 604/378 |
| 5,405,342 A | | 4/1995 | Roessler et al. |
| 5,507,735 A | | 4/1996 | Van Iten et al. ......... 604/385.1 |
| 5,558,633 A | * | 9/1996 | Phipps et al. ................. 604/20 |
| 5,599,337 A | * | 2/1997 | McCoy ................... 604/385.1 |

FOREIGN PATENT DOCUMENTS

| | | | | |
|---|---|---|---|---|
| EP | 0 525 778 A2 | | 2/1993 | |
| EP | 0 685 212 A2 | | 12/1995 | |
| FR | 2427795 | * | 2/1980 | .............. 604/385.1 |
| FR | 2653328 | * | 4/1991 | .............. 604/385.1 |
| GB | 1 295 493 | | 11/1972 | |
| GB | 2 191 098 A | | 12/1987 | |
| GB | 2 232 600 A | | 12/1990 | |
| GB | 2 232 600 | | 12/1990 | ........... A61F/13/15 |
| JP | 5-28327 | | 4/1993 | |
| JP | 5-33721 | | 5/1993 | |
| JP | 5-115506 | | 5/1993 | |
| WO | 9207535 | * | 5/1992 | .............. 604/385.1 |
| WO | 9406386 | * | 3/1994 | .............. 604/385.1 |
| WO | WO 94/16658 | | 8/1994 | ........... A61F/13/15 |
| WO | WO 94/16658 | | 10/1994 | |
| WO | WO 95/16422 | | 12/1994 | |
| WO | WO 95/16422 | | 6/1995 | ........... A61F/13/15 |
| WO | WO 96/19170 | | 12/1995 | |

* cited by examiner

BODY FITTING COMPOUND SANITARY NAPKIN

This is a continuation of application Ser. No. 08/636,711, filed on Apr. 23, 1996, which is a continuation of application Ser. No. 08/293,867, filed on Aug. 29, 1994 now abandoned.

FIELD OF THE INVENTION

The present invention relates to disposable sanitary napkins. As used herein, sanitary napkins are considered to be absorbent devices designed to be worn externally of the body by women, usually during their menstrual periods, and to receive and contain menses and other vaginal discharges. Disposable sanitary napkins are intended to be discarded after use and soiling rather than being cleaned and reused.

BACKGROUND OF THE INVENTION

In their simplest form, disposable sanitary napkins comprise an absorbent element (sometimes referred to as an absorbent core) interposed between a pervious body-contacting element (sometimes referred to as a topsheet or an overwrap) and an impervious protective barrier (sometimes referred to as a backsheet). The absorbent element is, of course, intended to receive and contain menses and other vaginal discharges. The body-contacting element is intended to provide more or less comfortable and dry-feeling contact with body surfaces while allowing free passage of fluids therethrough into the absorbent element. The protective barrier is intended to prevent menses or other vaginal discharges which are expelled or which escape from the absorbent element from soiling the user's garments.

In addition to the three functional elements mentioned above, disposable sanitary napkins are generally provided with means for supporting the device adjacent the user's crotch area, even as the user moves, where it can most effectively perform its intended function. Typically, sanitary napkins are provided with an adhesive attachment means for securing the device to the inner crotch area of the user's undergarments.

While previously known sanitary napkins do perform their intended function, each conventional design suffers from certain deficiencies in one or more of absorbency of body fluids, protection of the user's garments from soiling, and/or physical comfort to the user.

With respect to disposable sanitary napkins, at least two general classes presently exist. One such class is identified as being intended for the absorption of medium to high menstrual flows. These sanitary napkins offer a relatively high absorptive capacity. Absorptive capacity is commonly achieved by providing the sanitary napkin with a relatively thick and bulky absorbent member. While having a relatively high absorptive capacity, the bulkiness of the absorbent member may cause a certain degree of wearing discomfort.

A second class of sanitary napkins are intended for light or low menstrual flows and are commonly referred to as pantiliners or pantishields. Sanitary napkins of this class, as a group, are thinner, somewhat more flexible and generally more comfortable than those of the first class. However, sanitary napkins of the second class typically lack the absorptive capacity of sanitary napkins of the first class.

One attempt to provide the benefits of the previously described two classes of sanitary napkins into a single compound sanitary napkin is disclosed in commonly assigned U.S. Pat. No. 4,425,130 issued to DesMarais on Jan. 10, 1984. The compound sanitary napkin of DesMarais comprises a primary menstrual pad and a panty protector joined to one another at their corresponding ends in such a manner that the two constituents are free to move relative to one another along essentially their entire common length. The primary menstrual pad is intended to absorb the bulk of the bodily fluids discharged by the user, while the panty protector is intended to protect the user's garments from soiling. In use, the relative freedom of movement between the primary menstrual pad and the panty protector serves to maintain the primary menstrual pad adjacent the user's crotch region while the panty protector remains associated with the user's undergarment. While the relative freedom of movement between the primary menstrual pad and the panty protector serves to maintain the primary menstrual pad near the user's crotch region, this freedom of movement may lead to a lack of stability if the primary menstrual pad moves laterally beyond the side edges of the panty protector, providing an opportunity for soiling the user's undergarment.

Furthermore, the relative freedom of movement between the primary menstrual pad and the panty protector alone may be insufficient to capture bodily fluid as it exits the wearer's vaginal opening. The primary menstrual pad is preferably narrow enough to at least reside partially within the external genitalia. Optionally, the primary menstrual pad may be wider than the distance between the labia majora, but exhibits a lateral compression or conformability at relatively low forces, such as the forces exerted by the soft tissue of the female external genitalia, such that a portion of the primary menstrual pad is able to at least reside partially within the external female genitalia. By being conformable at relatively low forces, the primary absorbent member remains comfortable during use. In addition, the primary menstrual pad preferably exhibits a resilient recovery to enable the pad to conform to the body as the pad and body interface is subjected to shape changes.

As the primary menstrual pad is made narrower to fit the body, the panty protector preferably remains sufficiently wide enough to provide a stable attachment to the wearer's undergarment and to sufficiently cover the undergarment to protect it from soiling.

SUMMARY OF THE INVENTION

The present invention pertains to a compound sanitary napkin. The compound sanitary napkin comprises a primary absorbent member having a length and a width and a secondary absorbent member having a length and a width. The primary absorbent member and the secondary absorbent member have a common length. The primary absorbent member includes an absorbent core and a fluid pervious topsheet superimposed on said absorbent core. The secondary absorbent member includes a fluid pervious topsheet, a fluid impervious backsheet joined to said topsheet and an absorbent element positioned between the topsheet and the backsheet. The primary absorbent member is affixed to the secondary absorbent member by union means. The primary absorbent member exhibits a stationary resistance greater than or equal to about 50 grams. More preferably, the primary absorbent member exhibits a stationary resistance greater than or equal to 100 grams, most preferably greater than about 150 grams.

The primary absorbent member is affixed to the secondary absorbent member by union means in such a manner that the longest unattached distance between adjacent points of attachment is less than 75% of the common length.

Optionally, the primary absorbent member is affixed to the secondary absorbent member by union means in such a manner that the longest unattached distance between adjacent points of attachment is less than 50% of the common length. Optionally, the primary absorbent member is affixed to the secondary absorbent member by union means in such a manner that the longest unattached distance between adjacent points of attachment is less than 25% of the common length. Optionally, the primary absorbent member is affixed to the secondary absorbent member by union means extending along the entire common length of said primary absorbent member and said secondary absorbent member.

Optionally, the secondary absorbent member comprises an adhesive attachment means for securing the compound sanitary napkin in the crotch portion of the user's undergarment or panty. Optionally, the primary absorbent member comprises a resilient member. Optionally, the primary absorbent member comprises a fluid barrier. Optionally, the primary absorbent member may comprise two or more segments.

BRIEF DESCRIPTION OF THE DRAWINGS

While the specification concludes with claims particularly pointing out and distinctly claiming the present invention, it is believed that the present invention will be better understood from the following description in conjunction with the following drawings, in which like reference numbers identify identical elements and wherein:

DETAILED DESCRIPTION OF THE INVENTION

This invention is of a body fitting compound sanitary napkin which exhibits absorbency for bodily fluids, the protection of the user's garments from soiling, and physical comfort to the user. The term "sanitary napkin", as used herein, refers to an article which is worn by females adjacent to the pudendal region and which is intended to absorb and contain the various exudates which are discharged from the body (e.g., blood, menses, and urine) and which is intended to be discarded after a single use (i.e., it is not intended to be laundered or otherwise restored or reused). The term "compound sanitary napkin", as used herein, refers to a sanitary napkin comprised of separate constituents joined to one another to form a unitary structure. Interlabial devices which reside partially within and partially external of the wearer's vestibule are also within the scope of this invention. As used herein, the term "pudendal" refers to the externally visible female genitalia and is limited to the labia majora, the labia minora, the clitoris, and the vestibule.

Figure 1:
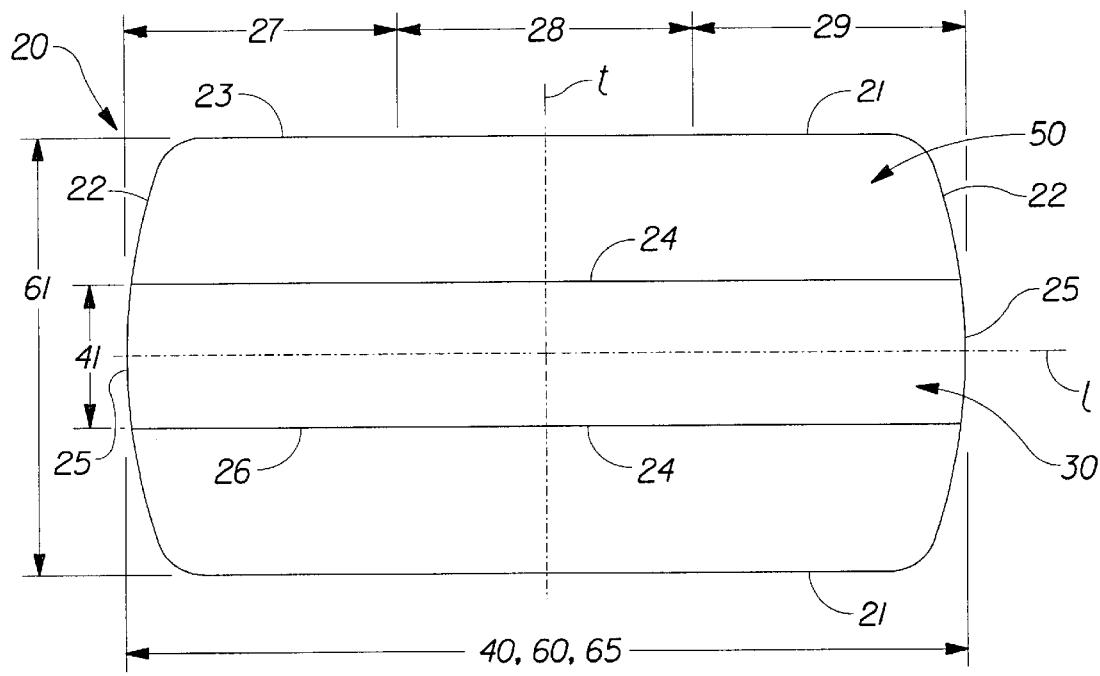
FIG. 1 is a top plan view of one embodiment of the compound sanitary napkin of the present invention.
Figure 2:
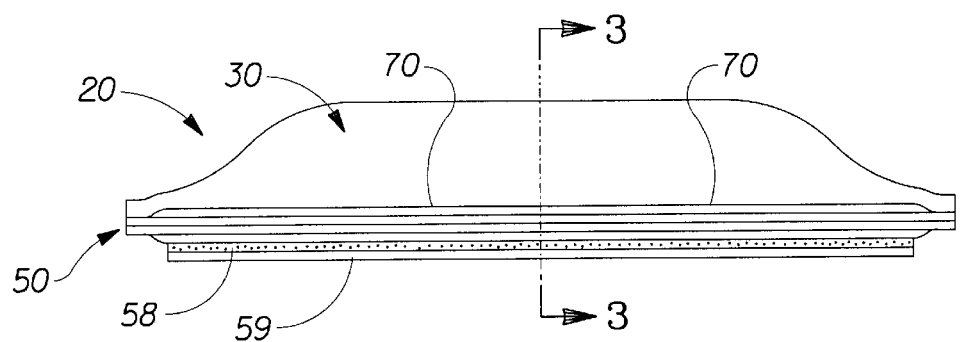
FIG. 2 is a side elevation view of the compound sanitary napkin shown in FIG. 1.
Figure 3:
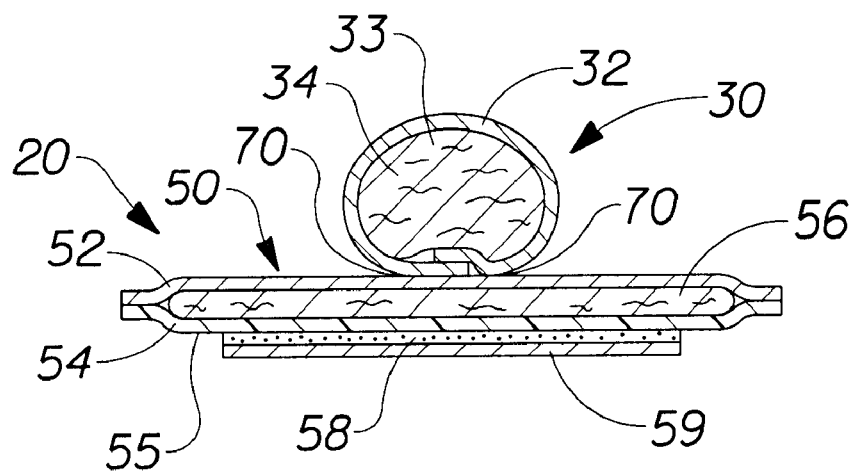
FIG. 3 is a cross-sectional view of the compound sanitary napkin shown in FIGS. 1 and 2 as taken along section line 3—3 of FIG. 2.

Referring now to FIGS. 1–3, there is shown one preferred embodiment of a compound sanitary napkin 20 of the present invention. As can be seen in FIGS. 1–3, the compound sanitary napkin 20 comprises a primary absorbent member 30 and a secondary absorbent member 50 joined together by union means 70.

The compound sanitary napkin has two surfaces, a body contacting or facing surface, and a garment facing or contacting surface. The primary and secondary absorbent members each have corresponding body facing and garment facing surfaces. The compound sanitary napkin 20 has two centerlines, a longitudinal centerline and a transverse centerline. The term "longitudinal", as use herein, refers to a line, axis or direction in the plane of the compound sanitary napkin that is generally aligned with (e.g., approximately parallel to) a vertical plane which bisects a standing wearer into left and right body halves when the compound sanitary napkin is worn. The terms "transverse" or "lateral", as used herein, are interchangeable, and refer, to a line, axis, or direction which lies within the plane of the compound sanitary napkin that is generally perpendicular to the longitudinal direction.

The primary absorbent member 30 has side edges 24 and end edges 25 which together form the periphery 26 of the primary absorbent member. The secondary absorbent member 50 has side edges 21 and end edges 22 which together form the periphery 23 of the secondary absorbent member and the compound sanitary napkin 20. The compound sanitary napkin 30 has a first end region 27, a central region 28, and a second end region 29.

The primary absorbent member 30 is, as its name implies, that constituent of the compound sanitary napkin 20 intended to absorb the bulk of bodily fluids discharged by the user. The primary absorbent member 30 comprises an absorbent means 33, such as absorbent core 34 and a liquid permeable topsheet or coverstock 32 superimposed on the absorbent core 34.

Preferably, the topsheet 32 is compliant, soft feeling, and non-irritating to the wearer's skin. Further, the topsheet 32 is liquid pervious, permitting liquid to readily penetrate through its thickness. A suitable topsheet 32 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers); or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, issued to Thompson on Dec. 30, 1975; U.S. Pat. No. 4,324,246, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird on Apr. 9, 1991. Each of these patents are incorporated herein by reference. The preferred topsheet for the primary absorbent member of the present invention is a formed film described in one or more of the above patents and marketed on sanitary napkins by The Procter & Gamble Company of Cincinnati, Ohio as "DRI-WEAVE".

In a preferred embodiment of the present invention, the body or exposed surface of the formed film topsheet is hydrophilic so as to help liquid transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, entitled "Absorbent Article Having a Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as described in U.S. Pat. No. 4,950,264 issued to Osborn on Aug. 21, 1990 and which is incorporated herein by reference.

The topsheet 32 may be associated with the absorbent core 34 in any suitable manner. Suitable manners include, but are not limited to associating the topsheet 32 with the absorbent core 34 with adhesives such as by spray-gluing or applying lines or spots of adhesives between the topsheet 32 and the absorbent core 34.

Alternatively, or additionally, the topsheet 32 may be associated with the absorbent core 34 by entangling the fibers of the absorbent core 34 with the topsheet 32, by fusing the topsheet 32 to the absorbent core 34 with a plurality of discrete individual fusion bonds, or by any means known in the art.

To insure proper fluid transfer between the topsheet 32 and the absorbent core 34 it is preferred that the topsheet be substantially continuously secured to the underlying absorbent core 34 throughout their common association or interface. By substantially continuously securing the topsheet 32 to the underlying absorbent core 34 the topsheet 32 will have a reduced tendency to separate from the absorbent core 34 during use. Separation of the absorbent core from the topsheet 32 may inhibit fluid transfer from the topsheet 32 into the underlying absorbent core 34.

The absorbent core 34 may be any absorbent means which is generally compressible, conformable, resilient, non-irritating to the wearer's skin and capable of absorbing and containing body exudates. The absorbent core 34 may be manufactured from a wide variety of liquid absorbent materials commonly used in disposable sanitary napkins, and other disposable absorbent articles. Examples of suitable absorbent materials include comminuted wood pulp (which is generally referred to as airfelt), creped cellulose wadding, modified cross-linked cellulose fibers (such as those described in U.S. Pat. No. 5,217,445 issued to Young, et al. on Jun. 8, 1993), capillary channel fibers (that is, fibers having intra-fiber capillary channels such as those described in U.S. Pat. No. 5,200,248 issued to Thompson, et al. on Apr. 6, 1993), absorbent foams (such as those described in U.S. Pat. No. 5,260,345, issued to DesMarais, et al. on Nov. 9, 1993 and U.S. Pat. No. 5,268,244 issued to DesMarais, et al. on Dec. 7, 1993), thermally bonded airlay materials (such as those material described in U.S. patent application Ser. No. 08/141,156, entitled "Catamenial Absorbent Structures Having Thermally Bonded Layers For Improved Handling of Menstrual Fluids and Their Use In Catamenial Pads Having Improved Fit and Comfort" filed in the name of Richards, et al. on Oct. 21, 1993 (P&G Case 5051)), absorbent sponges, synthetic staple fibers, polymeric fibers, hydrogel-forming polymer gelling agents, peat moss, or any equivalent materials or combinations of materials.

Suitable absorbent cores comprising foams are described in U.S. patent application Ser. Nos. 07/743,839, 07/743,950, 07/743,947 and 07/830,159 (P&G Case Nos. 4451, 4452, 4453, and 4453R) the first, third and fourth applications listed in the names of DesMarais, et al., and the second application filed in the name of Young, et al. The first three applications were filed on Aug. 12, 1991, and the fourth on Feb. 12, 1992. Additional cores comprising foams are described in European Application 0 293 208 B1. Absorbent cores comprising sponges are described in U.S. Pat. Nos. 3,512,530; and 3,954,493; and French Patent 2,203,827.

The total absorbent capacity of the absorbent core 34 should be compatible with the intended exudate loading for the compound sanitary napkin 20. Further, the absorbent capacity of the absorbent core 34 may be varied to accommodate wearers ranging in the expected amount of exudate fluid volume. For instance, a different absorbent capacity may be utilized for compound sanitary napkins intended for day time use as compared with those intended for night time use, or for compound sanitary napkins intended for use by teenage females as compared with those intended by more mature women.

Materials selected for use as the absorbent core 34 are preferably compliant, soft, comfortable, compressible and resilient to enhance body fit and comfort of the primary absorbent member. Preferably, the absorbent core is compressible such that the primary absorbent member will deform under relatively small forces that are experienced during normal use. In addition to being compressible, the materials comprising the absorbent core are preferably conformable such that the primary absorbent member is able to provide improved fit into and around the labia and perineum. While being generally compressible and conformable under relatively small forces, those forces exerted by the external female genitalia during use, it is also important that the primary absorbent member be sufficiently resilient such that when subjected to normal wearing forces it does not permanently collapse. Preferably, the primary absorbent member will be sufficiently resilient that it will conform to the contours of the body to provide intimate contact with the exposed genitalia of the female user. Intimate contact with the exposed female genitalia helps provide better fluid transfer from the user into the primary absorbent member without allowing fluid to bypass and/or run-off the primary absorbent member. While the resilient characteristics of the absorbent core 34 allow for improved fit, they must be balanced against the need for the product to be both soft and comfortable for the wearer.

In the embodiment illustrated in FIG. 3, the absorbent core 34 is comprised of airfelt. The airfelt absorbent core is manufactured in a generally cylindrical shape to provide the primary absorbent member 30 with a generally cylindrical shape.

Figure 3A:
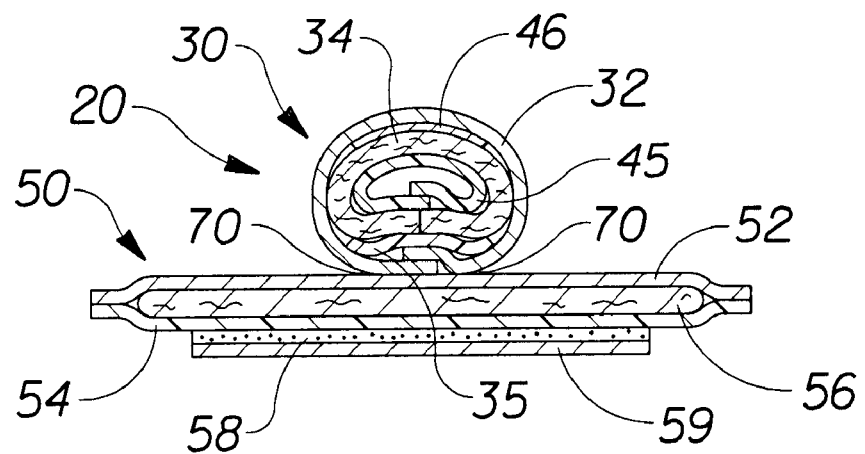
FIGS. 3A is a cross-sectional view of another embodiment of compound sanitary napkin of the present invention.

Referring now to FIG. 3A, there is shown a cross-sectional view taken along the transverse axis of another embodiment of a compound sanitary napkin of the present invention. In this embodiment, the absorbent core 34 is preferably comprised of an absorbent foam such as those described in the above referenced U.S. patent application Ser. Nos. 07/743,839, 07/743,950, 07/743,947 and 07/830, 159 (P&G Case Nos. 4451, 4452, 4453, and 4453R) the first, third and fourth applications listed in the names of DesMarais, et al., and the second application filed in the name of Young, et al. The absorbent foam core is folded or rolled such that it exhibits a generally circular cross-section. The folded core provides the primary absorbent member 30 with a generally cylindrical shape.

While the core 34 shown in FIGS. 3 and 3A has a generally circular cross-section, the absorbent core may be manufactured in a wide variety of shapes such as rectangular, triangular, oval, square, pentagonal, U-shaped, Z-folded, etc.

Optionally, the primary absorbent member 30 may comprise a resilient member 45 as is illustrated in FIG. 3A. The resilient member 45 may comprise a single member or a plurality of individual members. Suitable materials which may be used as the resilient member 45 include, but are not limited to, nylon, polypropylene, polyurethane, polyethylene, polyester, synthetic rubber, and other synthetic materials such as formed films, or natural materials such as rubber, sponges, and the like or any suitable material which is capable of resisting collapse under normal wearing conditions of sanitary napkins during use. The resilient member 45 may be manufactured in a wide variety of shapes such as rectangular, triangular, oval, square, pentagonal, U-shaped, Z-folded, etc.

The resilient member 45 may extend throughout the entire length of the primary absorbent member 30. The resilient member 45 may only extend through a portion of the length of the primary absorbent member 30. The resilient member 45 may be positioned within the first end region 27, the central region 28, the second end region 29 or any combination of the above. For example, the resilient member 45 may be positioned in either the first end region 27 or the second end region 29 of the primary absorbent member, in both the first end region 27 and the second end region 29 of the primary absorbent member, in the central region 28 of the primary absorbent member, or in the central region 28 and the end regions 27, 29 of the primary absorbent member.

Optionally, the primary absorbent member 30 can comprise a fluid barrier 35. The fluid barrier 35 tends to contain absorbed fluids within the absorbent core 34 and can be constructed from materials having the same properties as the liquid impervious backsheet on the secondary absorbent member 50 described hereinafter.

Optionally, the primary absorbent member 30 may comprise an acquisition layer 46 positioned between the topsheet 32 and the absorbent core 34. The acquisition layer 46 may serve several functions including improving wicking of exudates over and into the absorbent core 34. By improving the wicking of exudates, the acquisition layer provides a more even distribution of the exudates throughout the absorbent core. The acquisition layer 46 may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", filed Dec. 17, 1991 in the names of Cree, et al. Each of these references are incorporated herein by reference. In a preferred embodiment, the acquisition layer 46 may be joined with the topsheet by any of the conventional means for joining webs together, most preferably by fusion bonds as is more fully described in the above-referenced Cree application.

While the primary absorbent member can be generally of any cross-sectional shape in its unstressed condition it is preferably circular or oval in cross-section. The length 40 and the width 41 of the primary absorbent member 30 can be of any convenient dimension. The primary absorbent member 30, is preferably from about 2 to 35 cm long, more preferably from about 10 to 35 cm long, and most preferably from about 20 to 35 cm long. A particularly preferred primary absorbent member 30 has a length of about 24 cm. The primary absorbent member 30, is preferably from about 0.5 to 5 cm wide, more preferably from about 0.5 to about 4 cm wide, and most preferably from about 0.5 to about 3 cm wide.

Referring to FIGS. 1–3A, the second necessary constituent of the compound sanitary napkin of the present invention is the secondary absorbent member 50. The secondary absorbent member 50 preferably comprises a liquid permeable topsheet 52, a liquid impervious backsheet 54 joined with the topsheet 52, and an absorbent element 56 positioned between the topsheet 52 and the backsheet 54.

The topsheet 52 can be any fluid pervious material commonly used in sanitary napkins, disposable diapers, and the like. It can be any of the materials described above as being useful in the topsheet 32 of the primary absorbent member 30.

A preferred topsheet 52 comprises an apertured formed film. Apertured formed films are preferred for the topsheet because they are pervious to body exudates and yet non-absorbent and have a reduced tendency to allow liquids to pass back through and re-wet the wearer's skin. Thus, the surface of the formed film which is in contact with the body remains dry, thereby reducing body soiling and creating a more comfortable feel for the wearer. Suitable formed films are described in U.S. Pat. No. 3,929,135, issued to Thompson on Dec. 30, 1975; U.S. Pat. No. 4,324,246, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird on Apr. 9, 1991. Each of these patents are incorporated herein by reference. The preferred topsheet for the primary absorbent member of the present invention is a formed film described in one or more of the above patents and marketed on sanitary napkins by The Procter & Gamble Company of Cincinnati, Ohio as "DRI-WEAVE".

The absorbent element 56 can be any absorbent material commonly used in sanitary napkins, disposable diapers, and the like. It can be any of the materials described above as being useful in the absorbent core 34 of the primary absorbent member 30.

As a practical matter, most of the bodily fluids are absorbed by and are contained within the absorbent core of the primary absorbent member. One major function of the secondary absorbent member 50 is to protect the user's garments from soiling by absorbed fluids which may be expelled from the primary absorbent member or which may inadvertently bypass the primary absorbent member. Because the absorbent element 56 of the secondary absorbent member 50 performs a different function from that of the absorbent core 34, the absorbent element 56 can be, and most preferably is, somewhat thinner and less bulky than the absorbent core 34.

Because the absorbent element 56 has different requirements than does the absorbent core, it can be formed of different materials. For example, single or multiple plies of paper tissue as commonly used in paper toweling or toilet tissue can be used to form the absorbent element. Preferably, the absorbent element is formed of from about 1 to about 5 plies of paper tissue.

Preferably, the overall absorptive capacity of the absorbent element 56 is somewhat less than that of the absorbent core 34. Because the absorbent core 34 is preferably intended to absorb most or substantially all of the bodily fluids during use, its absorptive capacity will be somewhat if not significantly greater than that of the absorbent element 56.

Paper tissue comprising one or more plies having a basis weight of from about 24 to about 48 grams per square meter and an apparent density of from about 0.10 to about 0.12 grams per cubic centimeter as made by the process described in U.S. Pat. No. 3,301,746 issued to Sanford and Sisson on Jan. 31, 1967 and which patent is hereby incorporated herein by reference has been found to be quite satisfactory for use as the absorbent element 56. Wet strength resins and latex binders can be, and preferably are, used to provide additional strength to the paper tissue used in the absorbent element.

Paper tissue made by the process described in U.S. Pat. No. 3,994,771 issued to Morgan et al. on Nov. 30, 1976, and which patent is hereby incorporated herein by reference, can also be used to good advantage as the absorbent element 56.

Optionally, the secondary absorbent member may be manufactured without an absorbent element. Since most if not all of the bodily fluids are preferably absorbed by and are contained within the absorbent core of the primary absorbent member, the secondary absorbent member 50 need only to protect the user's garments from soiling by relatively small amounts of fluids which may be expelled from the primary absorbent member or which may inadvertently bypass the primary absorbent member. Accordingly, since the expected amounts of fluids which may come into contact with the secondary absorbent are relatively small, an absorbent element may not be necessary to contain the fluids within the secondary absorbent member and prevent them from soiling the user's garments.

The backsheet 54 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. In use, the backsheet 54 is interposed between the absorbent element 56 and the user's undergarments. The function of the backsheet 54 is to prevent exudates which may be expelled from or which inadvertently bypass the primary absorbent element and exudates absorbed and contained in the absorbent element 56 from contacting and soiling the user's undergarments. The backsheet 54 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.015 mm (2.0 mil). Exemplary polyethylene films are manufactured by Clopay Corporation of Cincinnati, Ohio under the designation P18-0401 and by Ethyl Corporation, Visqueen Division, of Terre Haute, Indiana, under the designation XP-39385. The backsheet is preferably embossed and/or matte finished to provide a more clothlike appearance. Further, the backsheet may permit vapors to escape from the absorbent element 56 (i.e., breathable) while still preventing exudates from passing through the backsheet.

Preferably, the secondary absorbent member 50 is provided with a support means or attachment means, such as adhesive attachment means 58. The adhesive attachment means 58 provides a means for securing the compound sanitary napkin 20 in the crotch portion of the user's undergarment or panty. Thus, a portion or all of the outer or garment surface 55 of the backsheet 54 is coated with adhesive. In a preferred embodiment, at least a portion of the adhesive 58 is positioned on the garment surface 55 of the backsheet 54 adjacent the longitudinal side edges 21 of the secondary absorbent member. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. The pressure-sensitive adhesive is typically covered with a removable release liner 59 in order to keep the adhesive from drying out or adhering to a surface other than the crotch portion of the panty prior to use. Suitable release liners are also described in the above referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/0 both of which are manufactured by the Akrosil Corporation of Menasha, Wis. The compound sanitary napkin 20 of the present invention is used by removing the release liner 50 and thereafter placing the sanitary napkin in a panty so that the adhesive 58 contacts the panty. The adhesive 58 maintains the sanitary napkin in its position within the panty during use.

The secondary absorbent member of the present invention is preferably relatively thin and flexible. The secondary absorbent member may have a caliper of about 1.9 millimeters. The caliper of the secondary absorbent member, or various regions thereof, is determined by the following test.

A comparator gauge, and specifically the Ames, Model 130 with dial indicator Model 482, available from the B.C. Ames Company of Waltham, Mass. is needed. The comparator gauge should have a circular comparator foot made of aluminum and having a weight of 10.0 grams and a contact surface of 5.16 square centimeters. The comparator gauge is zeroed. An 80.0 grams stainless steel weight is placed on the spindle extending above the comparator dial. The comparotor foot is raised and the secondary absorbent member, with any panty adhesive release paper being removed and the adhesive is sprinkled with corn starch, and the secondary absorbent member is placed garment surface down on the base plate. The secondary absorbent member is positioned on the base plate so that when the foot is lowered it is in the region of the secondary absorbent member for which the measurement is desired. Try to smooth out or avoid any wrinkles in the secondary absorbent member. Gently lower the foot onto the secondary absorbent member. Determine the secondary absorbent member caliper by reading the comparator dial 30 seconds after the foot comes in contact with the secondary absorbent member.

Preferably, the secondary absorbent member will have a caliper of less than about 3.0 millimeters, more preferably less than about 2.6 millimeters, more preferably less than about 2.2 millimeters, and most preferably less than about 2.0 millimeters.

The primary absorbent member of the present invention is preferably relatively conformable. It is preferred to keep the primary absorbent member relatively conformable so that it will readily fit into the labial grove during use. It has been found that a primary absorbent member having a width and or diameter dimension of about 3/8 inch is able to comfortably fit within at least a portion of the labial groove. While primary absorbent members have been described above as having widths or diameter dimensions greater than 3/8 inch, they too may fit within the labial groove if they are sufficiently conformable. It is not necessary that all of the primary absorbent member fit within the labial groove, however, a portion of the primary absorbent member is preferably capable of fitting within the labial groove. The conformability of a primary absorbent member, or various regions thereof, is determined by the following test.

A computer controlled tensile tester, and specifically the EME, Model 599A, available from the EME, Inc. of Newbury, Ohio is preferred, however, other tensile testers may be used. The tensile tester should have a pair of circular contact surfaces made of aluminum and having a diameter of 4.0 centimeters. The primary absorbent member is placed on the lower contact surface with one of its side edges residing downward and the opposing side edge facing upward toward the upper contact surface. The instrument is zeroed. The upper contact surface is lowered until there is a distance of 3/8 inch between the two opposing contact surfaces A conformity reading at 3/8 inch is taken to determine the force being exerted on the primary absorbent member.

The primary absorbent member may have a conformity at 3/8 inch of less than about 1.0 psi. Preferably, the primary absorbent member will have a conformity at 3/8 inch of less than about 0.5 psi, more preferably less than about 0.25 psi, and most preferably less than about 0.1 psi.

As shown in FIGS. 1–3, the secondary absorbent member can be of generally rectangular shape. Other suitable shapes include but are not limited to oval, hourglass, dog-bone, asymmetric, etc.

Figure 4:
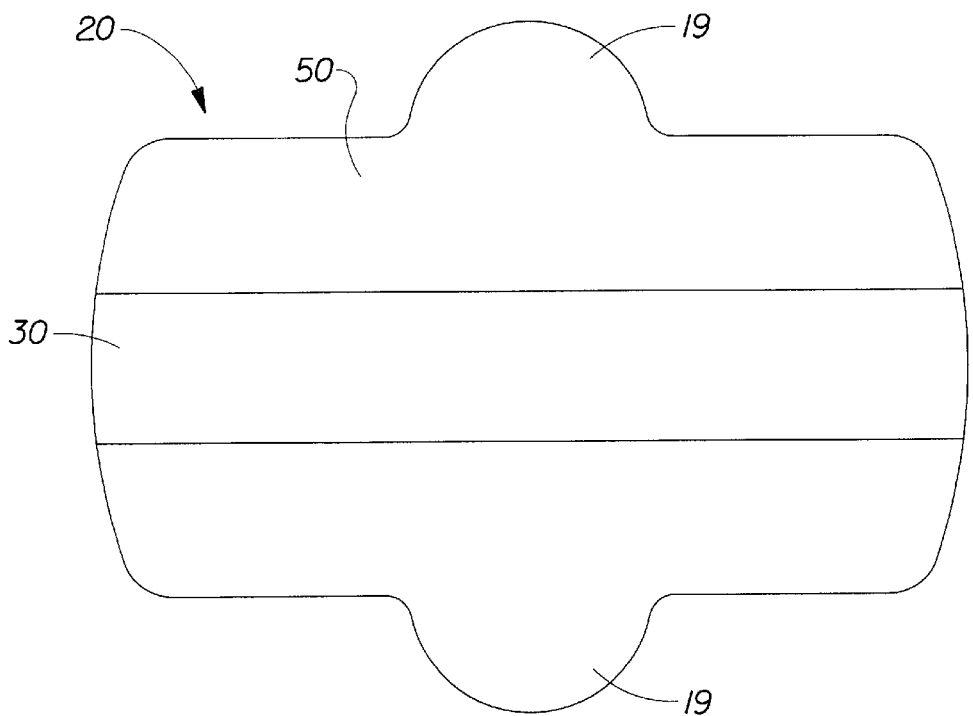
FIG. 4 is a top plan view of another embodiment of a compound sanitary napkin of the present invention.

Optionally, the secondary absorbent member 50 may have two flaps 19 each of which are adjacent to and extend laterally from the side edge of the absorbent core, as shown in FIG. 4. The flaps 19 are configured to drape over the edges of the wearer's panties in the crotch region so that the flaps are disposed between the edges of the wearer's panties and the wearer's thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment facing surface so that the flaps can be folded back under the panty and attached to the garment facing side of the panty. In this way, the flaps serve to keep the sanitary napkin properly positioned in the panty.

In a preferred embodiment, the flaps are comprised of the topsheet, absorbent element, and backsheet. Further, the flaps are preferably unitary to the laminae of the secondary absorbent element. In other words, the topsheet, absorbent element, and backsheet simply extend laterally outward to form the flaps. However, the flaps need not be unitary with the secondary absorbent member, but can be separate elements which are affixed to the secondary absorbent member. Further, the flaps can be comprised of a single substrate or other laminae configurations. It is recommended, however, that the flaps have a liquid impervious backsheet to prevent exudates which reach the flaps from soiling the edges of the wearer's panties.

Further, it is preferable that the flaps be provided with an absorbent member, at least to a point beyond the edges of the wearer's panties. Theoretically, only a relatively small amount of menses should reach the flaps, therefore, only a relatively small amount of absorbent material is desirable in the flaps. However, at least some absorbent material is recommended in order to prevent any exudates that reach the flaps from being able to flow further to unprotected areas. The absorbent material may be a tissue, or an extension of the absorbent element 56. However, the absorbent material in the flaps should be relatively highly flexible.

A number of sanitary napkins having flaps suitable or adaptable for use with the secondary absorbent member 50 of the compound sanitary napkin 20 of the present invention are disclosed in U.S. Pat. No. 4,687,478 issued to Van Tilburg on Aug. 18, 1987; U.S. Pat. No. 4,589,876 issued to Van Tilburg on May 20, 1986; and U.S. Pat No. 4,608,047 issued to Mattingly on Aug. 26, 1986. Each of these patents are incorporated herein by reference.

Optionally, the secondary absorbent member may comprise components that naturally wrap the sides of a wearer's panties. A sanitary napkin having components that naturally wrap the sides of a wearer's panties suitable for use with the secondary absorbent member of the compound sanitary napkin 20 of the present invention are disclosed in U.S. patent application Ser. No. 08/096,121, (P&G Case 4961) entitled "Absorbent Article having Panty Covering Components that Naturally Wrap the Sides of Panties", filed Jul. 22, 1993, in the names of Lavash, et al and U.S. patent application Ser. No. 08/277,733, now U.S. Pat. No. 5,558,633 entitled "Absorbent Articles Having Undergarment Covering Components with Zones of Extensibility", filed Jul. 20, 1994, in the names of Weinberger, et al. The disclosures of the preceding publications are incorporated herein by reference.

The individual components of the primary absorbent member 30 and the secondary absorbent member 50 may be comprised of components that are extensible (preferably, capable of stretching) particularly in the longitudinal direction when the compound sanitary napkin is worn. Preferably, the compound sanitary napkin is capable of elongating in the longitudinal direction between about 15% and about 40% of its unstretched length. This extensibility provide better in-use fit, comfort, and decreased staining when the compound sanitary napkin is affixed to the wearer's undergarments.

Preferably, the secondary absorbent member is comprised of components that are also extensible in the lateral direction when the compound sanitary napkin is worn. Preferably, the compound sanitary napkin is capable of elongating in the lateral direction between about 15% and about 40% of its unstretched length.

The topsheet for both the primary absorbent member and the secondary absorbent member may comprise an elastic, three-dimensional, fluid pervious, polymeric web as disclosed in U.S. U.S. patent application Ser. No. 07/936,195 filed Aug. 25, 1992 in the names of Curro, et al., and which is incorporated herein by reference.

A particularly preferred extensible backsheet is an extended adhesive film known as Formula #198–388 manufactured by the Findley Adhesives Company of Wauwatosa, Wis.

Sanitary napkins having extensible components are described in U.S. patent application Ser. Nos. 07/915,133 and 07/915,284 both filed Jul. 23, 1992, in the name of Osborn, et al. (PCT Publication Nos. WO 93/01785 and 93/01786, both published Feb. 4, 1993). The disclosures of the preceding publications are incorporated herein by reference.

Referring now to FIG. 1, the secondary absorbent member 50 preferably has a length 60 and a width 61. The secondary absorbent member is preferably from about 20 to 40 cm long, more preferably from about 25 to 35 cm long, and most preferably is about 30 cm long.

While it can be of generally any cross-section in its unstressed condition, the primary absorbent member is preferably rectangular in cross-section. The secondary absorbent member is preferably from about 5 to 15 cm in width, more preferably from about 5 to 10 cm in width, and most preferably from about 5 to 8 cm in width. The thickness of the secondary absorbent member 50, as shown in cross-section in FIGS. 2 and 3, is generally somewhat less than its width.

Because the primary absorbent member performs different functions than that of the secondary absorbent member, the properties and characteristics of the materials forming the primary absorbent member and a secondary absorbent member may be distinct from one another. One major function of the primary absorbent member is to absorb and contain bodily fluids. In addition, the primary member is preferably sized and shaped such that it will fit within the labia. Accordingly, the width and/or diameter of the primary absorbent member should be sized such that it will reside at least partially within the labia. That is, a portion of the primary absorbent member will preferably fit within the labia during use. Since the exposed female genitalia, including the labia, are generally referred to as soft body tissue, it is important that the materials comprising and the primary absorbent member be comfortable and relative soft such that they are non-irritating and/or uncomfortable for the user. In contrast, one major function of the secondary absorbent member is to protect the user's garments from soiling by absorbed fluids which may be expelled from the primary absorbent member or which may inadvertently bypass the primary absorbent member. Because the secondary absorbent member performs a different function from that of the primary absorbent member, its dimensions and properties may be somewhat different than that of the primary absorbent member.

Preferably, the width of the secondary absorbent member is at least 1.5 times the width of the primary absorbent member. More preferably, the width of the secondary absorbent member is at least 2 times the width of said primary absorbent member. Most preferably, the width of the secondary absorbent member is in the range from about 3 to about 8 times the width of the primary absorbent member.

Preferably, the secondary absorbent member is about the same length as the primary absorbent member while the compound sanitary napkin is in an unstressed condition. However, it is quite possible for the secondary absorbent member to be somewhat longer than the primary absorbent member and still function effectively.

Referring now to FIG. 1, it can be seen that the primary absorbent member 30 and the secondary absorbent member 50 share a common length 65. The common length, refers to the length that the primary absorbent member and the secondary member have in common.

To form the compound sanitary napkin of the present invention, the primary absorbent member and the secondary absorbent member are joined by union means generally indicated as 70 in FIGS. 2 and 3.

The precise nature of the union means is immaterial so long as the union means selected serves to join the primary absorbent member and the secondary absorbent member into the compound sanitary napkin of the present invention with sufficient tenacity that the primary absorbent member and the secondary absorbent member are not disconnected during use. Union means such as adhesive attachment with well known hot melt and pressure sensitive adhesives are quite satisfactory. If the nature of the components selected to construct the constituents of the compound sanitary napkin so permit, heat welding, ultrasonic welding, or a combination of both heat and ultrasonic welding can be used.

The primary absorbent member may be affixed to said secondary absorbent member by union means in such a manner that the longest unattached distance between adjacent points of attachment is less than 75% of said common length. Optionally, the primary absorbent member is affixed to said secondary absorbent member by union means in such a manner that the longest unattached distance between adjacent points of attachment is less than 50% of said common length. Optionally, the primary absorbent member is affixed to said secondary absorbent member by union means in such a manner that the longest unattached distance between adjacent points of attachment is less than 25% of said common length. Optionally, the primary absorbent member is affixed to the secondary absorbent member by union means extending along substantially the entire common length.

Figure 5:
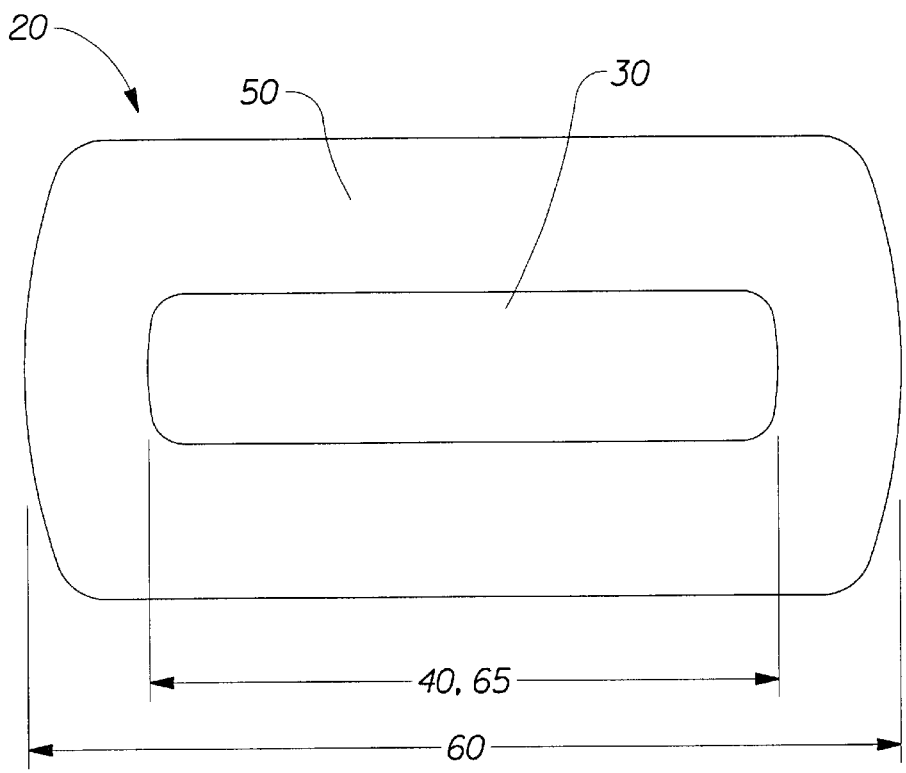
FIG. 5 is a top plan view of another embodiment of a compound sanitary napkin of the present invention.

Referring now to FIG. 5, there is shown another preferred embodiment of a compound sanitary napkin 20 of the present invention. The primary absorbent member 30 has a length 40 that is somewhat less than the length 60 of the secondary absorbent member 50. Accordingly, the common length 65 corresponds to the length 40 of the primary absorbent member 30.

Referring now to FIG. 3, it can be seen that topsheet 32 completely encases the absorbent core 34 of the primary absorbent member 30. In this embodiment, the topsheet 32 for the primary absorbent member 30 is separate and distinct from the topsheet 52 for the secondary absorbent member 50.

Figure 6:
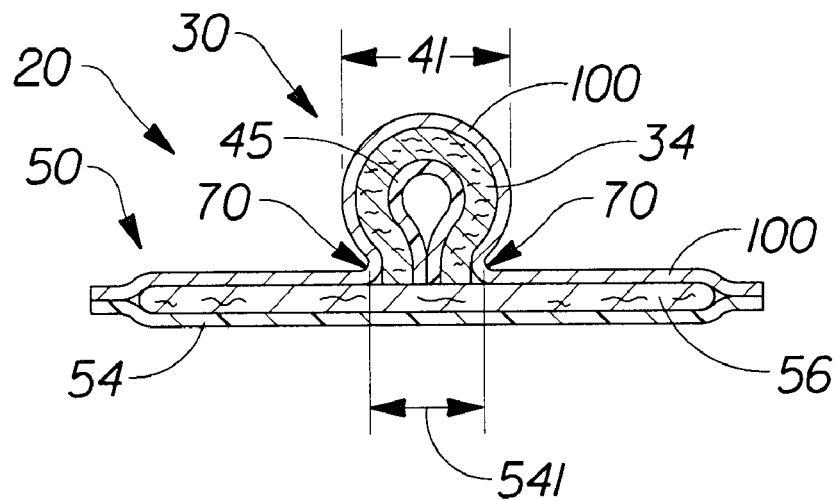
FIG. 6 is a cross-sectional view of another embodiment of a compound sanitary napkin of the present invention.

Optionally, the topsheet for the primary absorbent member 30 and the secondary absorbent member 50 may be made of a single web of material, such as topsheet 100 as seen in FIG. 6. In this embodiment topsheet 100 is used for the topsheet on both the primary absorbent member 30 and the secondary absorbent member 50. In the embodiment of FIG. 6 the topsheet 100 serves as a union means 70 connecting the primary absorbent member and the secondary absorbent member together. The compound sanitary napkin may also include additional union means to connect the primary absorbent member to the secondary absorbent member. Suitable additional union means include but are not limited to adhesives and fusion bonds. The primary absorbent member 30 has a width 41. The compound sanitary napkin has a union means width 541, which is the distance across the union means 70. The union means width 541 is less than the width of the primary absorbent member. Preferably, the union means width 541 is less than 75% of the width of the primary absorbent member 30. More preferably, the union means width 541 is less than 50% of the width of the primary absorbent member 30. Most preferably, the union means width 541 is less than 25% of the width of the primary absorbent member 30.

As can be seen in FIG. 6, the absorbent core 34 is positioned between the topsheet 100 and the resilient member 45 of the primary absorbent member 30. The resilient member 45 has a substantially U-shaped cross-section and causes the primary absorbent member 30 to have a generally U-shaped cross-section.

The resiliency of the resilient member 45 is preferably not affected by the presence of body exudates absorbed by and contained within the absorbent core. The sustained resiliency of the resilient member 45 permits the primary absorbent member 30 to maintain intimate contact with the body of the wearer during use.

Figure 6A:
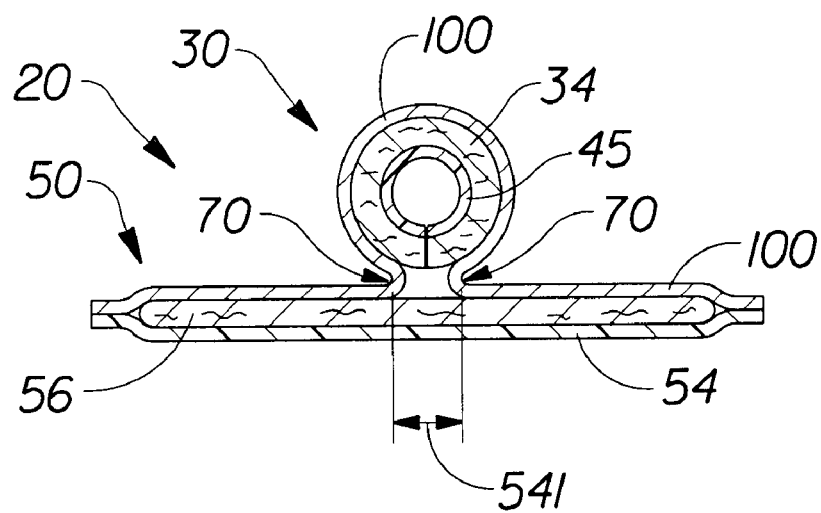
FIG. 6A is a cross-sectional view of another embodiment of a compound sanitary napkin of the present invention.

Referring now to FIG. 6A, the resilient member 45 and the primary absorbent member 30 have a generally circular or oval cross-sectional configuration.

Preferably, the primary absorbent member exhibits a "stationary resistance" sufficient enough to provide enhanced performance. As used herein, the term "stationary resistance" refers to the resistance exhibited by the primary absorbent member to forces applied to the primary absorbent member within the central region such that the side edges of the primary absorbent member do not extend beyond the side edges of the secondary absorbent member. In other words, the stationary resistance describes the relative movement of the primary absorbent member compared to the secondary absorbent member. It is preferred, that the side edges of the primary absorbent member do not extend beyond the side edges of the secondary absorbent member even under relatively high forces. By keeping the side edges of the primary absorbent member within the side edges of the secondary absorbent member, under relatively high forces, the opportunity for fluid to bypass or be expelled from the primary absorbent member and onto a surface other than the secondary absorbent member, for example, the user's skin or undergarments, is substantially reduced.

The apparatus necessary for the determination of the stationary resistance includes a scale and a resistance member. A suitable scale is a Sartorius Universal Balance. The resistance member is a cylindrical rod having a diameter of 1 inch (2.54 cm). The resistance member preferably has a length of about 6 inches (15.24 cm). The resistance member may be made of any suitable material capable of withstanding the forces during the stationary resistance procedure. Suitable materials include but are not limited to, steel, aluminum, plastic, and wood, etc.

Figure 7:
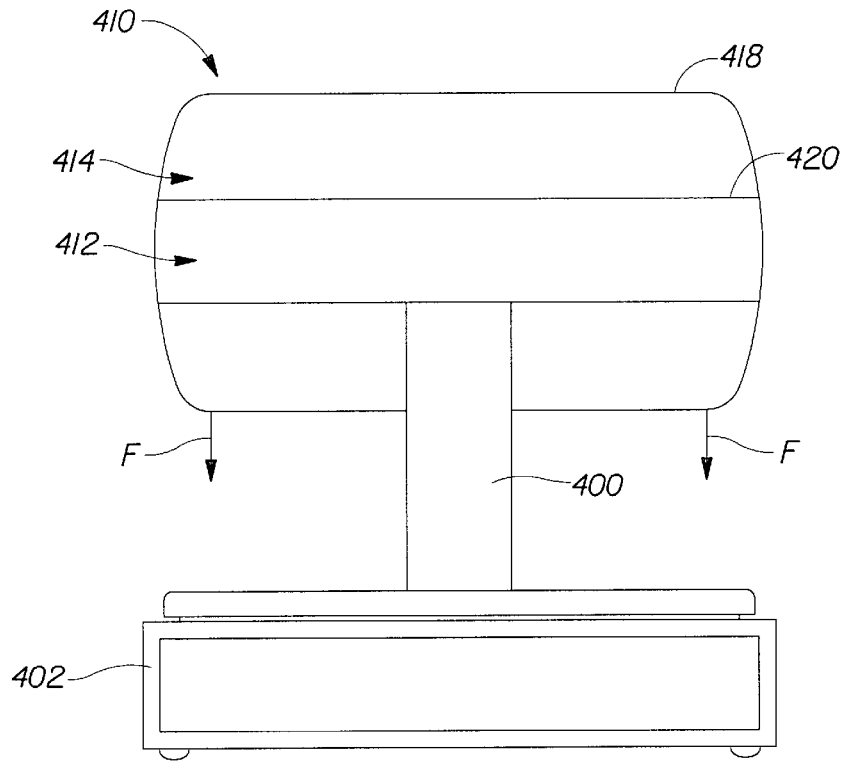
FIGS. 7 and 8 are simplified schematic views of the stationary resistance test procedure.
Figure 8:
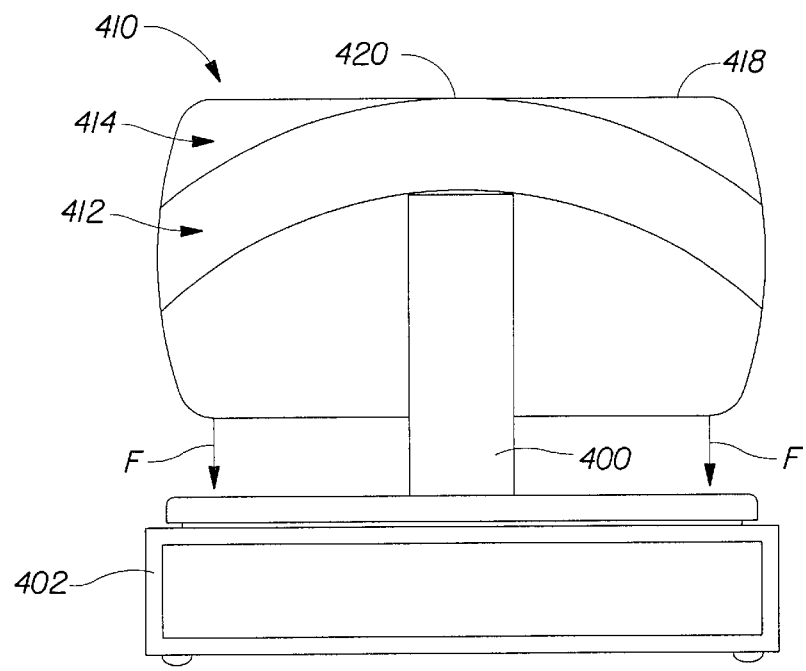

The procedure for the stationary resistance test is as follows: referring now to FIGS. 7 and 8, a resistance member 400 is placed on scale 402. Scale 402 is then tared to zero the scale. A compound sanitary napkin such as napkin 410 having primary absorbent member 412 and secondary absorbent member 414 is placed on the testing apparatus such that primary absorbent member 412 resides on resistance member 400. The backsheet portion of the secondary absorbent member 414 should be aligned substantially parallel to the axis of the resistance member 400. A force, generally indicated as F in FIGS. 7 and 8 is applied to each end of the secondary absorbent member 414. Force should be applied until the side edge 420 of the primary absorbent member is equal with the side edge of the secondary absorbent member 418 as viewed substantially perpendicular to the topsheet portion of the secondary absorbent member 414. Once the side edges of the respective primary absorbent member and secondary absorbent member are aligned, a force reading the nearest gram is recorded. This reading indicates the stationary resistance of the primary absorbent member.

The primary absorbent member may exhibit a stationary resistance greater than about 600 grams. Preferably, the primary absorbent member exhibits a stationary resistance greater than or equal to 50 grams, more preferably greater than or equal to 100 grams, and most preferably greater than or equal to 150 grams.

Several specific non-limiting compound sanitary napkin embodiments are shown in FIGS. 9–17.

Figure 9:
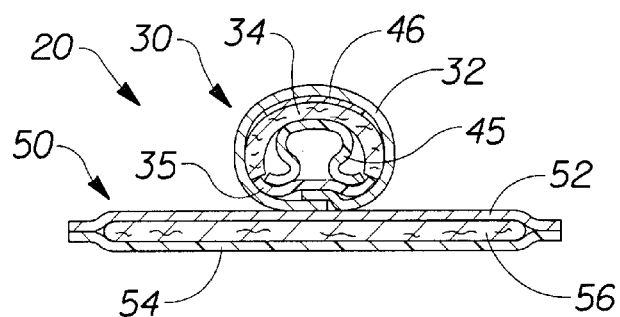
FIG. 9 is a cross-sectional view of another embodiment of a compound sanitary napkin of the present invention.

An example of a primary absorbent member having a Z-folded resilient member 45 is shown in FIG. 9. As can be seen in FIG. 9, the absorbent core 34 is preferably positioned between the topsheet 32 and the resilient member 45. Positioning the absorbent core 34 between the topsheet 32 and the resilient member 45 helps to provide intimate contact between the absorbent core 34 and the topsheet 32. Intimate contact between the topsheet and the absorbent core through bonding or pressure applied by the resilient member is described to promote fluid transfer from the topsheet into the underlying absorbent core.

In some embodiments, it may be desirable to have a resilient member 45 which is capable of absorbing bodily fluids. Such materials may include but are not limited to absorbent foams and sponges.

Figure 10:
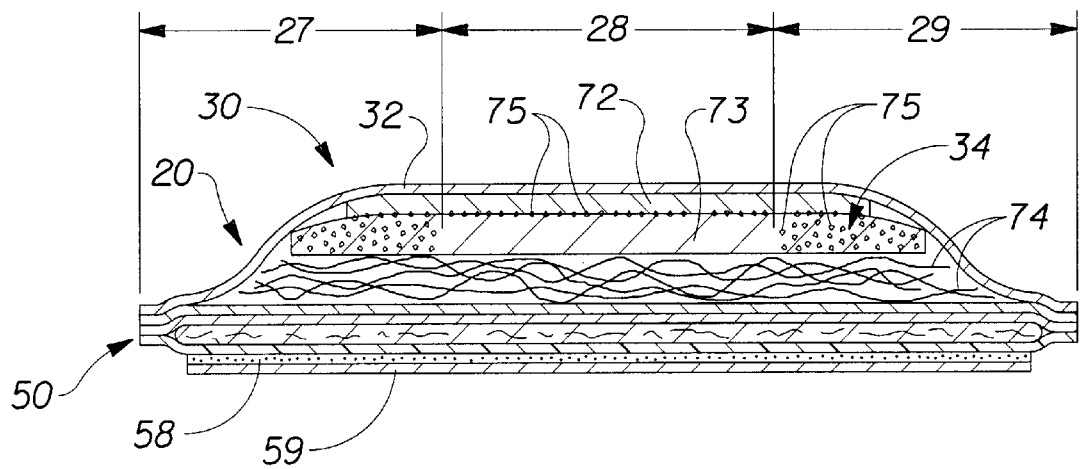
FIG. 10 is a cross-sectional view taken along the longitudinal axis of a compound sanitary napkin of the present invention.

Referring now to FIG. 10 there is shown a cross-sectional view taken along the longitudinal axis of another embodiment of a compound sanitary napkin 20 of the present invention. The primary absorbent member 30 includes an absorbent core 34 comprised of a relatively low density layer 72, a relatively high density layer 73, a plurality of resilient fibers 74, and absorbent gelling material 75 dispersed on and within the high density layer 73. The absorbent gelling material 75 is dispersed primarily within the first and second end regions 27, 29 of the primary absorbent member 30. The relatively low density layer 72 is preferably comprised of a thermally bonded airlaid material. The relatively high density layer 73 is preferably comprised of a thermally bonded airlaid material. The resilient fibers are preferably polyester capillary channel fibers.

Figure 11:
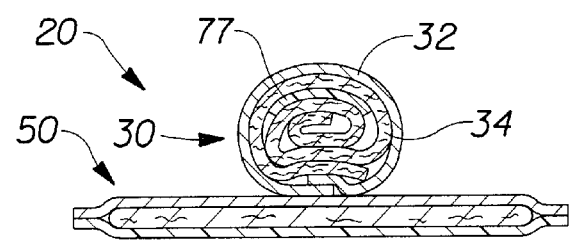
FIG. 11 is a cross-sectional view of another embodiment of a compound sanitary napkin of the present invention.

Referring now to FIG. 11, there is shown a cross-sectional view of another embodiment of a compound sanitary napkin 20 of the present invention. The absorbent core 34 comprises a carded nonwoven layer of capillary channel fibers. The nonwoven layer is rolled onto itself to form multiple layers. Preferably, a masking element 77 is positioned within the nonwoven layer of capillary channel fibers. A suitable masking element is a fluid impervious film. Another suitable masking element is a formed film. Optionally, absorbent materials such as absorbent gelling materials may be incorporated into the nonwoven layer of capillary channel fibers.

While the nonwoven layer of capillary channel fibers is shown in FIG. 11 as having a generally circular cross-section, the layer of capillary channel fibers may be manufactured in a wide variety of shapes such as rectangular, triangular, oval, U-shaped, Z-folded, etc.

Figure 12:
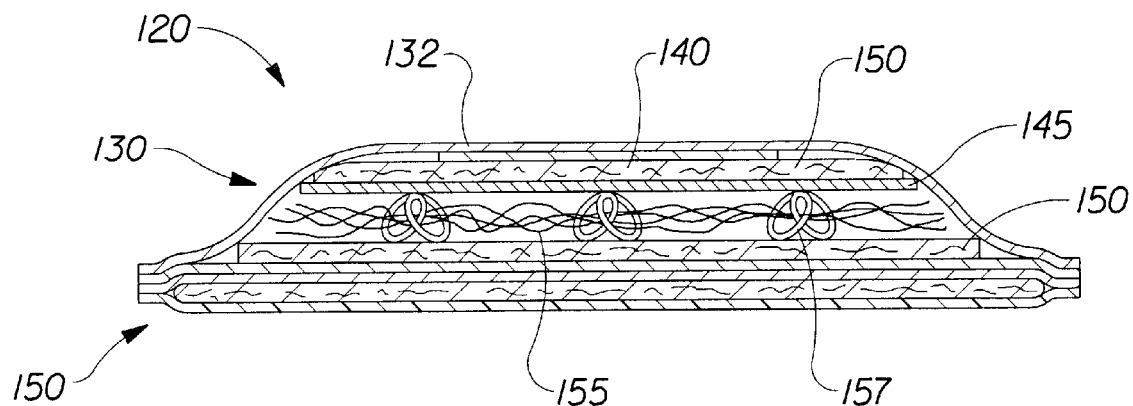
FIG. 12 is a cross-sectional view taken along the longitudinal axis of a compound sanitary napkin of the present invention.

Referring now to FIG. 12, there is shown another embodiment of a compound sanitary napkin 120. The compound sanitary napkin 120 comprises a primary absorbent member 130 and a secondary absorbent member 150. The primary absorbent member 130 includes an apertured formed film topsheet 132, an acquisition element 140, a distribution element 145, absorbent core layer 150, a first resilient member 155 and second resilient member 157. The first resilient member 155 extends substantially throughout the length of the primary absorbent member 130. The first resilient member 155 preferably comprises polymeric capillary channel fibers as described in U.S. Pat. No. 5,200,248 issued to Thompson, et al. on Apr. 6, 1993. The second resilient member 157 preferably comprises nylon monofilament arranged in a substantially circular cross-section secured to one another near the acquisition element 140 and near the interior surface of the absorbent core 150. As can be seen in FIG. 12, the secondary resilient members 157 are positioned substantially in the central portion of the primary absorbent member 130.

The primary absorbent member 30 may include a resilient member 45 similar to the internal shaping component disclosed in U.S. patent application Ser. No. 08/225,441, (P&G Case 5109R), entitled "Sanitary Napkin having an Internal Shaping Component", filed Apr. 8, 1994, in the name of Carl L.Bergman. The disclosure of the above referenced application is incorporated herein by reference.

Figure 13:
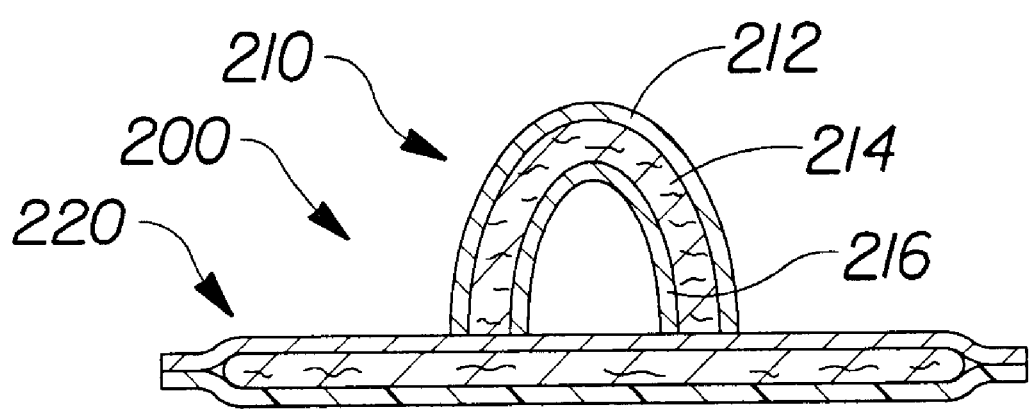
FIG. 13 is a cross-sectional view of another embodiment of a compound sanitary napkin of the present invention.

In FIG. 13 there is shown another preferred embodiment of a compound sanitary napkin 200. The compound sanitary napkin 200 comprises a primary absorbent member 210 and a secondary absorbent member 220. The primary absorbent member 210 preferably comprises a topsheet 212, an absorbent core 214 and a resilient member 216. As can be seen in FIG. 8, the resilient member 216 has a substantially inverted V-shaped cross-section. Accordingly, the primary absorbent member 210 likewise has a substantially inverted V-shaped cross-section. Preferably, the resilient member 216 extends throughout substantially the entire length of the primary absorbent member 210.

Figure 14:
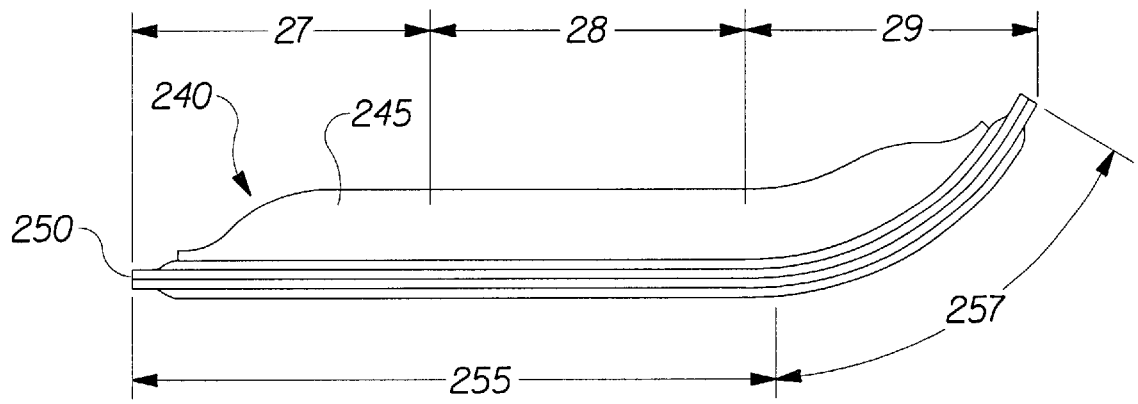
FIG. 14 is a side elevational view of another embodiment of a compound sanitary napkin of the present invention.

Referring now to FIG. 14 there is shown another preferred embodiment of a compound sanitary napkin 240 of the present invention. Compound sanitary napkin 240 preferably comprises a primary absorbent member 245 and a secondary absorbent member 250. As can be seen in FIG. 14 the compound sanitary napkin 240 preferably has a substantially horizontal segment 255 and an upwardly curved segment 257. The horizontal segment 255 resides within first end portion 27 and central portion 28. Upwardly curved segment 257 resides within second end portion 29. Preferably, the upwardly curved segment 257 includes a tensioning means which provides ample tension to create the curvature in the second segment 257. Suitable tensioning means include but are not limited to a tensioned topsheet, an elastic material, thread, film, or any suitable means to provide the desired tension. Optionally, the segment residing within the first end portion 27 may also be upwardly curved.

Figure 15:
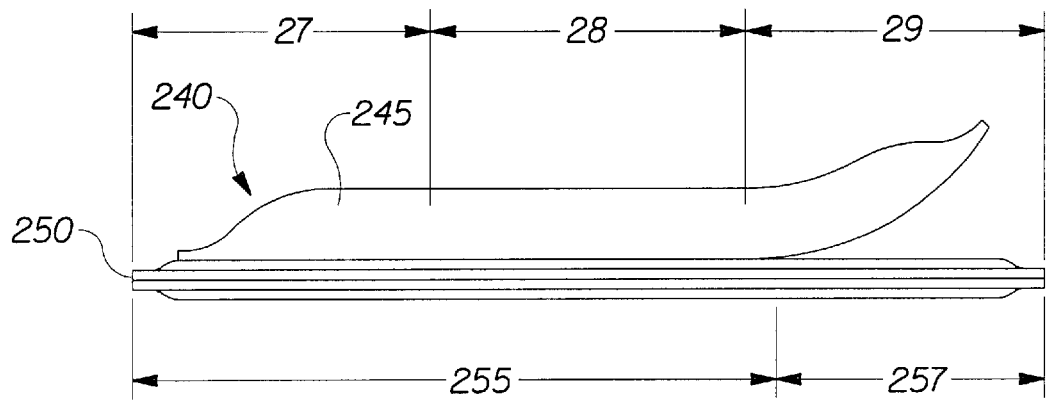
FIG. 15 is a side elevation view of another embodiment of a compound sanitary napkin.

As seen in FIG. 15 the primary absorbent member 245 and the secondary absorbent member 250 are joined together throughout their entire common length. That is, they are joined together throughout segments 255 and 257. Optionally, they may be joined together in the first segment 255 and may separate from one another in the rear segment 257 as shown in FIG. 15. In this embodiment, the secondary absorbent element 250 remains substantially in the same plane throughout segments 255 and 257 while in an unstressed condition. The primary absorbent member 245 positioned within the second segment 257 curves upward away from and separates itself from the secondary absorbent member 250. The segment 257 generally corresponds with the second end portion 29. The primary absorbent member may also curve upwardly within the first end portion 27.

Figure 16:
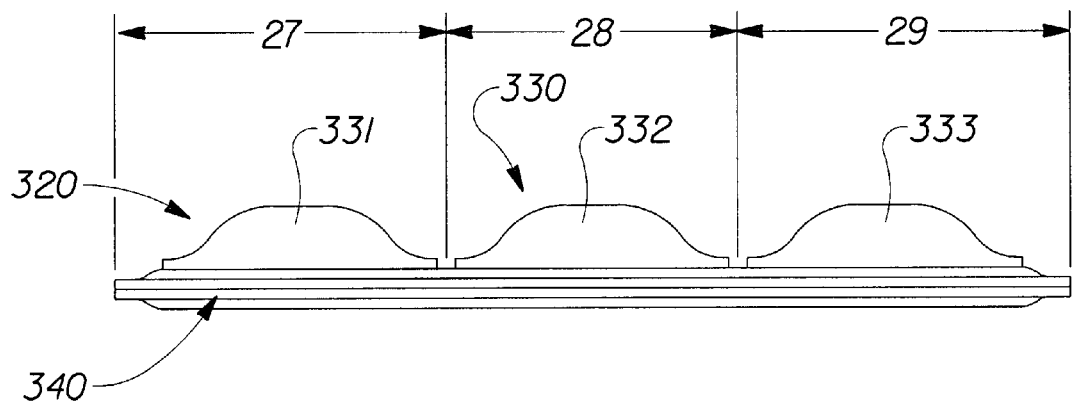
FIG. 16 is a side elevational view of another embodiment of a compound sanitary napkin of the present invention.
Figure 17:
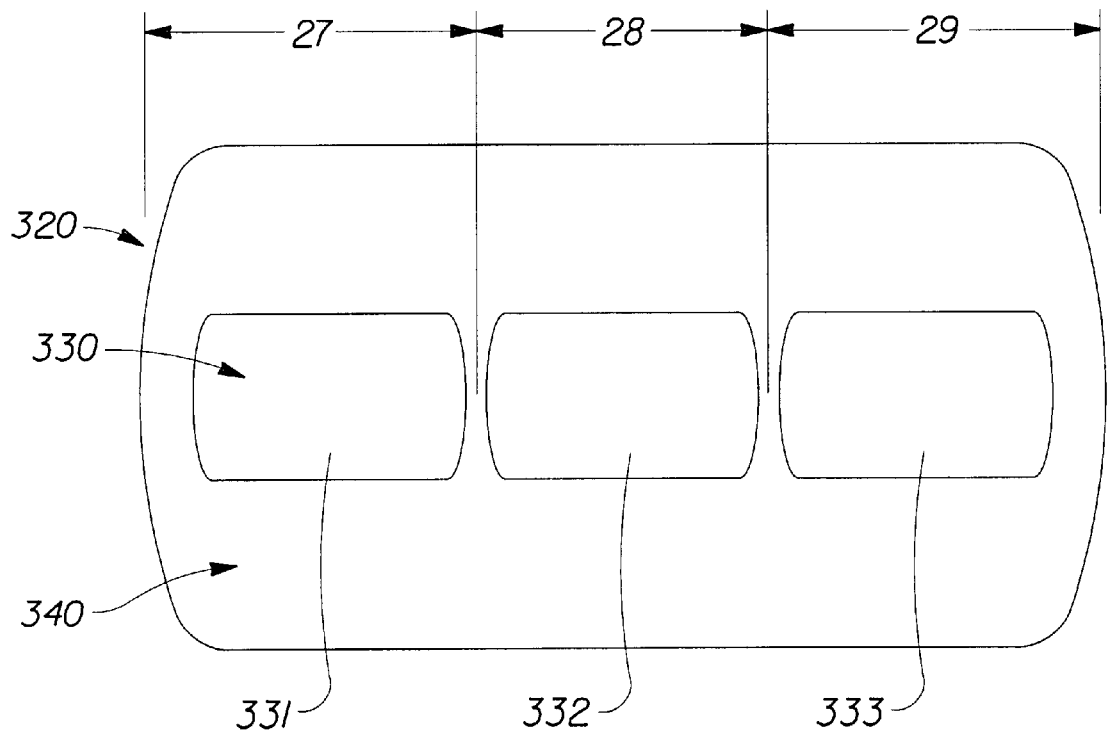
FIG. 17 is a top plan view of the compound sanitary napkin of FIG. 11.

Referring now to FIGS. 16 and 17, there is shown another embodiment of the compound sanitary napkin 320 of the present invention. The compound sanitary napkin 320 comprises a segmented primary absorbent member 330 and a secondary absorbent member 340. The primary absorbent member comprises individual absorbent components 331, 332 and 333. As shown in FIGS. 16 and 17, segment 331 lies wholly within first end region 27, segment 332 resides wholly within central region 28, and segment 333 resides wholly within second end region 39. Optionally, the primary absorbent member may comprise two components which extend from the end regions 27 and 29 into the central region 28. Optionally, the primary absorbent member may be comprised of 4 or more individual components. While the primary absorbent member having multiple components is shown in FIGS. 16 and 17 as extending throughout the length of the compound sanitary napkin, it may be desirable to have some segments or some regions of the compound sanitary napkin having no primary absorbent element. For example, the first end region 27 and central region 28 may comprise an primary absorbent constituent where second end region 29 comprises only a secondary absorbent member. Moreover, the primary absorbent members within the various regions may be designed to perform specific functions and therefore may be made of materials to perform the desired functions. For example, the primary absorbent segment 332 within central region 28 may contain a greater capacity of absorbent material than that of segments 331 or segments 333 since segment 332 will likely be positioned such that it will receive the bodily fluids directly, whereas the elements or segment 331 or 333 will likely receive and therefore have less capacity than that of the segment 332 within central region 28.

It may be desirable to provide a compound sanitary napkin having a primary absorbent member with varying degrees of width or caliper throughout its length. For example, the primary absorbent member may be relatively thicker in the central region as opposed to the end regions. Alternatively, the primary absorbent member may be relatively thinner in the central region as opposed to the end regions.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable compound sanitary napkin having a longitudinal direction and a transverse direction, said compound sanitary napkin comprising: an uppermost disposable primary absorbent member having a length oriented in said longitudinal direction, a width, and an absorptive capacity and a lowermost disposable secondary absorbent member having a length oriented in said longitudinal direction, a width, and an absorptive capacity, the length of said secondary absorbent member being at least equal to the length of said primary absorbent member, the absorptive capacity of said primary absorbent member being greater than the absorptive capacity of said secondary absorbent member, said primary absorbent member including an absorbent core and a first fluid pervious topsheet superimposed on said absorbent core, said primary absorbent member being sized to fit at least partially within the labial groove of a wearer during use, said secondary absorbent member including a second fluid pervious topsheet, a fluid impervious backsheet joined to said second topsheet and an absorbent element positioned between said second topsheet and said backsheet, said primary absorbent member being joined to said secondary absorbent member by union means extending substantially continuously along the length of said primary absorbent member.

2. The compound sanitary napkin of claim 1, wherein said secondary absorbent member comprises adhesive attachment means.

3. The compound sanitary napkin of claim 1, wherein said topsheet on said primary absorbent member comprises a formed film.

4. The compound sanitary napkin of claim 1, wherein said topsheet on said secondary absorbent member comprises a formed film.

5. The compound sanitary napkin of claim 1, wherein said topsheet on said primary absorbent member comprises a nonwoven fabric.

6. The compound sanitary napkin of claim 1, wherein said topsheet on said secondary absorbent member comprises a nonwoven fabric.

7. The compound sanitary napkin of claim 1, wherein said primary absorbent member comprises a fluid barrier.

8. The compound sanitary napkin of claim 1, wherein said primary absorbent member comprises a resilient member.

* * * * *